United States Patent
Jia et al.

(10) Patent No.: US 8,664,294 B2
(45) Date of Patent: Mar. 4, 2014

(54) SELF ETCH ALL PURPOSE DENTAL CEMENT COMPOSITION AND METHOD OF USE THEREOF

(75) Inventors: Weitao Jia, Wallingford, CT (US); Shuhua Jin, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 199 days.

(21) Appl. No.: 13/048,479

(22) Filed: Mar. 15, 2011

(65) Prior Publication Data

US 2011/0171608 A1 Jul. 14, 2011

Related U.S. Application Data

(63) Continuation-in-part of application No. 11/360,314, filed on Feb. 23, 2006, now Pat. No. 7,906,564.

(51) Int. Cl.
A61K 6/083 (2006.01)
A61C 5/00 (2006.01)

(52) U.S. Cl.
USPC .................. 523/116; 523/118; 433/228.1

(58) Field of Classification Search
USPC .................. 523/116, 118; 433/228.1
See application file for complete search history.

(56) References Cited

U.S. PATENT DOCUMENTS

| | | |
|---|---|---|
| 4,148,988 A | 4/1979 | Masuhara et al. |
| 4,306,913 A | 12/1981 | Mabie et al. |
| 4,503,169 A | 3/1985 | Randklev |
| 4,544,359 A | 10/1985 | Waknine |
| 4,547,531 A | 10/1985 | Waknine |
| 4,593,054 A | 6/1986 | Asmussen et al. |
| 4,659,751 A | 4/1987 | Bowen |
| 4,691,045 A | 9/1987 | Fukuchi et al. |
| 4,719,149 A | 1/1988 | Aasen et al. |
| 4,802,950 A | 2/1989 | Croll |
| 4,880,660 A | 11/1989 | Aasen et al. |
| 5,061,183 A | 10/1991 | Nicholson |
| 5,171,763 A | 12/1992 | Ohno et al. |
| 5,256,065 A | 10/1993 | Nicholson |
| 5,260,476 A | 11/1993 | Ohno et al. |
| 5,264,513 A | 11/1993 | Ikemura et al. |
| 5,276,068 A | 1/1994 | Waknine |
| 5,348,988 A | 9/1994 | Suh et al. |
| 5,444,104 A | 8/1995 | Waknine |
| 5,525,648 A | 6/1996 | Aasen et al. |
| 5,756,560 A | 5/1998 | Antonucci et al. |
| 5,865,623 A | 2/1999 | Suh |
| 5,925,690 A | 7/1999 | Fuchigami et al. |
| 5,954,996 A | 9/1999 | Discko, Jr. |
| 5,969,000 A | 10/1999 | Yang et al. |
| 6,004,390 A | 12/1999 | Pflug et al. |
| 6,013,694 A | 1/2000 | Jia et al. |
| 6,071,983 A | 6/2000 | Yamamoto et al. |
| 6,147,137 A | 11/2000 | Jia |
| 6,217,644 B1 | 4/2001 | Matsunae et al. |
| 6,270,562 B1 | 8/2001 | Jia |
| 6,291,548 B1 | 9/2001 | Akahane et al. |
| 6,312,667 B1 | 11/2001 | Trom et al. |
| 6,355,704 B1 | 3/2002 | Nakatsuka et al. |
| 6,403,676 B1 | 6/2002 | Jia et al. |
| 6,417,246 B1 | 7/2002 | Jia et al. |
| 6,572,693 B1 | 6/2003 | Wu et al. |
| 6,653,365 B2 | 11/2003 | Jia |
| 6,673,958 B2 | 1/2004 | Tiba et al. |
| 6,730,715 B2 | 5/2004 | Jia |
| 6,759,449 B2 | 7/2004 | Kimura et al. |
| 6,815,470 B2 | 11/2004 | Ibaragi et al. |
| 6,939,900 B2 | 9/2005 | Ario et al. |
| 7,166,651 B2 | 1/2007 | Qian |
| 7,214,726 B2 | 5/2007 | Qian |
| 7,304,096 B2 | 12/2007 | Han et al. |
| 2002/0082317 A1 | 6/2002 | Lyons et al. |
| 2003/0055124 A1 | 3/2003 | Klee et al. |
| 2003/0207960 A1 | 11/2003 | Jia |
| 2004/0054027 A1 | 3/2004 | Lyons et al. |
| 2004/0156795 A1 | 8/2004 | Nemoto et al. |
| 2004/0229973 A1 | 11/2004 | Sang et al. |
| 2004/0235981 A1 | 11/2004 | Qian |
| 2005/0014861 A1 | 1/2005 | Qian |
| 2005/0020720 A1 | 1/2005 | Dickens et al. |
| 2005/0049326 A1 | 3/2005 | Park et al. |
| 2005/0192374 A1 | 9/2005 | Jia et al. |
| 2005/0277706 A1 | 12/2005 | Han et al. |
| 2007/0197683 A1 | 8/2007 | Jia et al. |
| 2007/0299157 A1 | 12/2007 | Sang et al. |
| 2008/0242761 A1 | 10/2008 | Jia et al. |

OTHER PUBLICATIONS

S. Venz and B. Dickens: Modified Surface-Active Monomers for Adhesive Bonding to Dentin; J Dent Res 72 (3):582-586, Mar. 1993.

*Primary Examiner* — Tae H Yoon

(74) *Attorney, Agent, or Firm* — Wood, Herron & Evans, LLP

(57) ABSTRACT

A self etching, dental cement composition is provided having the advantage of not requiring a separate etching and bonding step. The cement composition comprises a polymerizable (meth)acrylate trimellitic acid/anhydride, a phosphoric acid (meth)acrylate, a hydroxyalkyl(meth)acrylate, copolymerizable multi-functional (meth)acrylate monomers, a diluent, fillers, and a curing system. These cement compositions are prepared as a two-paste system that is combined prior to use.

20 Claims, No Drawings

SELF ETCH ALL PURPOSE DENTAL CEMENT COMPOSITION AND METHOD OF USE THEREOF

CROSS REFERENCE TO RELATED APPLICATION

This application is a continuation-in-part of U.S. patent application Ser. No. 11/360,314 filed Feb. 23, 2006 and entitled SELF ETCH ALL PURPOSE DENTAL CEMENT COMPOSITION, METHOD OF MANUFACTURE, AND METHOD OF USE THEREOF, now U.S. Pat. No. 7,906,564, the disclosure of which is incorporated herein by reference in its entirety as if completely set forth herein below.

FIELD OF THE INVENTION

This invention relates to dental resin cement compositions comprising polymerizable (meth)acrylate resins, and the use of such resins for restorative dentistry without the need for a separate etching/bonding step.

BACKGROUND OF THE INVENTION

Methods and compositions for improving the adhesion of resins to hard tissue, i.e., dentin or enamel, is an ongoing goal in the dental arts. Improved adhesion leads to longer lasting restorations and reduced tooth sensitivity. Numerous methods for preparing teeth for the application of a dental restorative material (such as a sealant, filling material, cementation of indirect dental restorations or the like) have accordingly been developed, including acid etch and priming steps.

Acid etchants are commonly used to remove a smear layer and demineralize the tooth surfaces so as to promote effective mechanical bonding of the restorative material. However, the use of an etchant has a disadvantage in that it must be washed off after application, requiring the time-consuming procedure of application, washing, and drying. A further disadvantage of etchants is the perception that use of strong etchants can increase dental sensitivity in some patients.

In addition to acid etch procedures, adhesive strength is also improved by use of a primer. Primers are generally surface-active compounds that exhibit both an affinity for dentin and adhesive resin systems and participate in the polymerization process, thereby promoting adhesion between the primarily hydrophilic dentin and the predominantly hydrophobic polymeric adhesives or monomers from which they are formed. Primers are applied to dentin in solution form, commonly used solvents including acetone, ethanol, water, and various mixed solvent systems. While effective for promoting bonding, primers however are often applied using an additional step.

Current resin cement materials used for the cementation of dental restorations made from metal alloy, ceramic/porcelain, or composite material require a separate bonding procedure to ensure sufficient and effective bonding of the dental restoration to the tooth. Often a separate procedure including etching and applying a bonding adhesive to the tooth or restoration is required, rendering the cementation procedure time consuming and more complex.

Conventional luting cements such as glass ionomer cement, zinc phosphate cement, and polycarboxylate cement are typically used for cementing metal restorations without a separate bonding step. However, the luting cements are not suitable for cementing composite or ceramic restorations. Additionally, the bonding ability of the luting cements to tooth structure is poor.

There accordingly remains a need in the art for improved dental cement materials providing improved adhesion to a tooth surface and a dental substrate, and yet which can be applied in a fewer number of steps.

SUMMARY OF THE INVENTION

The above-described drawbacks and disadvantages are alleviated by a self-etching and bonding dental resin cement composition comprising a polymerizable (meth)acrylate trimellitic acid/anhydride; a phosphoric acid (meth)acrylate; a hydroxyalkyl(meth)acrylate; copolymerizable multi-functional (meth)acrylate monomers; a diluent; fillers; and a curing system. These cement compositions are prepared as a two-paste system that is combined prior to use.

Specifically, a self-etching and bonding dental resin cement composition comprises a two paste system that is combined prior to use, wherein a catalyst paste comprises a first polymerizable resin composition, a first filler, and a peroxide free radical polymerization initiator; and a base paste comprises a second polymerizable resin composition, a second filler, a free radical polymerization accelerator, and optionally a photoinitiator. Further, the first polymerizable resin composition comprises, based on 100 weight percent, about 5 to about 50% of a (meth)acrylate trimellitic acid/anhydride, about 5 to about 20% of a phosphoric acid (meth)acrylate, about 5 to about 25% of a hydroxyalkyl(meth)acrylate, and the balance being one or more first copolymerizable multi-functional (meth)acrylates, and the second polymerizable resin composition comprises one or more second copolymerizable ethylenically unsaturated multi-functional (meth)acrylates and a diluent.

The self-etching and bonding dental resin cement composition provides even further advantages over the art, as all etching and bonding can be performed in one step without the need for the use of an etchant or a separate bonding adhesive. Furthermore, the self-etching and bonding dental resin cement composition can be self-curable, or both self-curable and light curable, i.e., dual-curable.

In accordance with the method of use, the self-etching and bonding dental resin cement composition is physically contacted with the tooth structure or a tooth restoration, the tooth restoration is then adhered to the tooth surface, and the cement composition is allowed to cure.

DETAILED DESCRIPTION

Described herein are self-etching and bonding dental resin cement compositions that will, in one operation, etch the tooth surface, i.e. remove dentin smear and etch/dissolve calcium minerals from the surface of the tooth structure, and bond a tooth restoration to the tooth. As the cement composition is self-etching and bonding, the resin cement coating forms a reliable bond with the tooth structure and a tooth restoration. The composition can accordingly be used without intermediate adhesion steps.

Specifically, a self-etching and bonding dental resin cement composition comprises a two paste (catalyst-base) system that is combined prior to use, wherein a catalyst paste comprises a first polymerizable resin composition, a first filler, and a peroxide free radical polymerization initiator; and a base paste comprises a second polymerizable resin composition, a second filler, a free radical polymerization accelerator, and optionally a photoinitiator. The first polymerizable resin composition of the catalyst paste comprises, based on 100 weight percent, about 5 to about 50% of a (meth)acrylate trimellitic acid/anhydride, about 5 to about 20% of a phosphoric acid (meth)acrylate, about 5 to about 25% of a hydroxyalkyl(meth)acrylate, and the balance being one or more first copolymerizable multi-functional (meth)acrylates. The second polymerizable resin composition comprises one or more second copolymerizable multi-functional (meth) acrylates and a diluent.

Exemplary polymerizable (meth)acrylate trimellitic acid/anhydrides include 4-(meth)acryloyloxymethyltrimellitic acid and the anhydride thereof; 4-(meth)acryloyloxyethyltrimellitic acid (4-MET) and an anhydride thereof (4-META); 4-(meth)acryloyloxypropyltrimellitic acid and an anhydride thereof; or a combination comprising at least one of the foregoing.

The polymerizable (meth)acrylate trimellitic acid/anhydrides may be synthesized, for example, from the reaction of a hydroxy-containing (meth)acrylate monomer and an aromatic compound comprising anhydride or trimellitic acid functionality or their synthetic equivalents (e.g., a trimellitic acid halide, for example chloride). Exemplary synthetic methods are described in U.S. Published Application, 2005/0192374A1 incorporated herein by reference in its entirety.

The polymerizable (meth)acrylate trimellitic acid/anhydride is present in the catalyst paste at about 5 to about 50 weight percent, for example about 20 to about 40 weight percent based on the total weight of the first polymerizable resin composition. As used herein, "polymerizable resin" includes any compound that can copolymerize with the (meth)acrylate functionality of the polymerizable (meth) acrylate trimellitic acid/anhydride, such as compounds comprising ethylenically unsaturated groups, and the like.

As used herein, the term "(meth)acrylate" is intended to encompass both acrylate and methacrylate groups.

Optionally, the polymerizable (meth)acrylate trimellitic acid/anhydride may also be present in the base paste in an amount of about 1 to about 40 weight percent, for example about 2 to about 30 weight percent, by further example about 3 to about 20 weight percent, and by yet further example about 4 to about 10 weight percent based on the total weight of the second polymerizable resin composition.

The self-etching and bonding dental resin cement composition further comprises a phosphoric acid (meth)acrylate in the catalyst paste, at about 5 to about 20 weight percent, for example about 10 to about 15 weight percent based on the total weight of the first polymerizable resin composition. For example, glyceryldimethacrylate phosphate (GPDM) may be used. Rather than using about 40-80% of a (meth)acrylate carboxylic acid/anhydride as in U.S. Pat. No. 7,906,564, the present composition substitutes a portion of the acid/anhydride with a smaller percentage of the more acidic phosphoric acid (meth)acrylate. As can be seen from the formulas and acidities below, the two resin components are structurally compatible and GPDM has a higher acidity and can thus be used in a smaller amount in place of a portion of 4-META, for example, to maintain the same overall acidity for the first polymerizable resin composition.

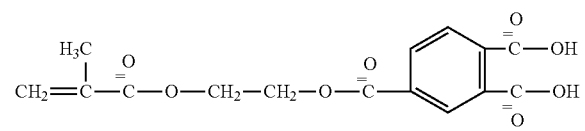

4-META pH is about 3-4.
Ref. pKa of benzoic acid is 4.2

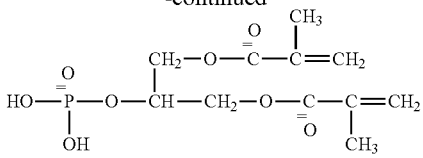

GPDM, pH is about 1-2
Ref. pKa1 of phosphoric acid is 2.15

The phosphoric acid (meth)acrylate in combination with the (meth)acrylate trimellitic acid/anhydride has the effect of lowering the hydroscopic expansion of the cement material by reducing the hydrophilic content, but also unexpectedly maintains stability with a peroxide-amine self-curing free radical initiator system.

The self-etching and bonding dental resin cement composition further comprises a hydroxyalkyl(meth)acrylate in the catalyst paste, at about 5 to about 25%, for example about 10 to about 20 weight percent based on the total weight of the first polymerizable resin composition. For example, hydroxyalkyl(meth)acrylates include 2-hydroxyethyl(meth)acrylate, 2-hydroxypropyl(meth)acrylate, and 4-hydroxybutyl(meth) acrylate, specifically HEMA. Limiting the HEMA content also has the effect of lowering the hydroscopic expansion of the cement material by reducing the hydrophilic content in the resin.

The balance of the first polymerizable resin composition of the catalyst paste includes one or more copolymerizable multi-functional (meth)acrylates. The multi-functional (meth)acrylate may be monomeric, oligomeric, or polymeric, and has a (meth)acrylate functionality that is copolymerizable with the polymerizable (meth)acrylate trimellitic acid/anhydride, specifically two or more (meth)acrylate functionalities. The multi-functional (meth)acrylates include, for example, urethane(meth)acrylates, including urethane dimethacrylate (UDMA); polyurethane(meth)acrylates, including polyurethane dimethacrylate (PUDMA); diurethane dimethacrylates, including diurethane di(meth)acrylate (DUDMA); polycarbonate di(meth)acrylates, including the polycarbonate dimethacrylate (PCDMA) disclosed in U.S. Pat. Nos. 5,276,068 and 5,444,104 to Waknine, which is the condensation product of two parts of a hydroxyalkyl-methacrylate and 1 part of a bis(chloroformate); ethoxylated bisphenol A di(meth)acrylates including ethoxylated bisphenol A dimethacrylate (EBPDMA) as disclosed in U.S. Pat. No. 6,013,694 to Jia et al.; ethoxylated trimethylolpropane tri(meth)acrylates, specifically having about 10 to about 30 ethoxy groups; the diglycidyl(meth)acrylate adducts of Bisphenol A, including 2,2'-bis[4-(3-methacryloxy-2-hydroxy propoxy)-phenyl]propane (BisGMA); ethylene glycol (meth)acrylates, including diethylene glycol(meth)acrylate, tri(ethylene glycol) di(meth)acrylate, specifically tri(ethylene glycol) dimethacrylate (TEGDMA), and tetra(ethylene glycol) di(meth)acrylate; propylene glycol (meth)acrylates, both 1,2- and 1,3-, including dipropylene glycol(meth)acrylate, tri(propylene glycol) di(meth)acrylate, and tetra(propylene glycol) di(meth)acrylate; diol di(meth)acrylates such as 1,4-butanediol di(meth)acrylate, dodecane diol di(meth) acrylate, and 1,6-hexanediol di(meth)acrylate; glycerol di(meth)acrylates; trimethylolpropane di- and tri-(meth) acrylates; pentaerythritol di- and tri-(meth)acrylates; or any combination thereof.

In one example, the balance of the first polymerizable resin composition is TEGDMA, for example in an amount of about 10 to about 35 weight percent based on the total weight of the first polymerizable resin composition. In another example, the balance of the first polymerizable resin composition is a combination of UDMA and TEGDMA, for example each in an amount of about 10 to about 35 weight percent based on the total weight of the first polymerizable resin composition.

The self-etching and bonding dental resin cement composition further comprises one or more copolymerizable multi-functional (meth)acrylates present in the second polymerizable resin composition of the base paste. The copolymerizable multi-functional (meth)acrylates may be monomeric, oligomeric, or polymeric, and have a (meth)acrylate functionality that is copolymerizable with the polymerizable (meth)acrylate trimellitic acid/anhydride, specifically two or more (meth)acrylate functionalities. The copolymerizable multi-functional (meth)acrylates include, for example, urethane(meth)acrylates, including urethane dimethacrylate (UDMA); polyurethane(meth)acrylates, including polyurethane dimethacrylate (PUDMA); diurethane dimethacrylates, including diurethane di(meth)acrylate (DUDMA); polycarbonate di(meth)acrylates, including the polycarbonate dimethacrylate (PCDMA) disclosed in U.S. Pat. Nos. 5,276,068 and 5,444,104 to Waknine, which is the condensation product of two parts of a hydroxyalkyl-methacrylate and 1 part of a bis(chloroformate); ethoxylated bisphenol A di(meth)acrylates including ethoxylated bisphenol A dimethacrylate (EBPDMA) as disclosed in U.S. Pat. No. 6,013,694 to Jia et al.; ethoxylated trimethylolpropane tri(meth)acrylates, specifically having about 10 to about 30 ethoxy groups; the diglycidyl(meth)acrylate adducts of Bisphenol A, including 2,2'-bis[4-(3-methacryloxy-2-hydroxy propoxy)-phenyl]propane (BisGMA); or a combination comprising at least one of the foregoing.

The total amount of the second copolymerizable multi-functional (meth)acrylates present in the base paste can be about 50 to about 95 weight percent, for example about 60 to about 90 weight percent and, in a further example, about 70 to about 80 weight percent based on the total weight of the second polymerizable resin composition.

The self-etching and bonding dental resin cement composition further comprises a diluent monomer in the second polymerizable resin composition of the base paste. Diluent monomers may be used to increase the surface wettability of the composition and/or to decrease the viscosity of the polymerization medium. The diluent monomers may or may not also be copolymerizable multi-functional (meth)acrylates, but are generally categorized as diluents due to lower viscosity. Suitable diluent monomers include, for example: hydroxyalkyl(meth)acrylates, for example 2-hydroxyethyl (meth)acrylate (HEMA), 2-hydroxypropyl(meth)acrylate, and 4-hydroxybutyl(meth)acrylate, specifically HEMA; ethylene glycol mono- and di-(meth)acrylates, including ethylene glycol(meth)acrylate, diethylene glycol(meth)acrylate, tri(ethylene glycol) di(meth)acrylate, specifically tri(ethylene glycol) dimethacrylate (TEGDMA), and tetra(ethylene glycol) di(meth)acrylate; propylene glycol mono- and di-(meth)acrylates, both 1,2- and 1,3-, including propylene glycol(meth)acrylate, dipropylene glycol(meth)acrylate, tri(propylene glycol) di(meth)acrylate, and tetra(propylene glycol) di(meth)acrylate; diol di(meth)acrylates such as 1,4-butanediol di(meth)acrylate, dodecane diol di(meth)acrylate, and 1,6-hexanediol di(meth)acrylate; glycerol mono- and di-(meth)acrylates; trimethylolpropane mono-, di-, and tri-(meth)acrylates; pentaerythritol mono-, di-, and tri-(meth) acrylates; phenyl glycidyl ether(meth)acrylate; or a combination comprising at least one of the foregoing. Those diluents that are also copolymerizable multi-functional (meth)acrylates may be especially useful in the base paste, for example TEGDMA.

The total amount of diluent in the base paste can be about 5 to about 50 weight percent, for example about 10 to about 40 weight percent, and in a further example about 20 to about 30 weight percent based on the total weight of the second polymerizable resin composition. In one example, the second polymerizable resin composition of the base paste includes a mixture of UDMA and TEGDMA, where both are copolymerizable multi-functional methacrylates and TEGDMA is further a diluent.

The self-etching and bonding dental resin cement composition further contains a curing system, which generally can include polymerization initiators; polymerization accelerators; ultraviolet light absorbers; antioxidants; and/or other additives known in the art depending upon whether the cement composition is formulated for self-cure or dual-cure.

The self-cure composition can be cured without the use of radiation activation. Such curing systems include a free radical polymerization initiator in the catalyst paste, such as a peroxide in an amount of about 0.1 to about 5.0 parts per hundred based on the total of the polymerizable materials of the first polymerizable resin composition. Exemplary free radical polymerization initiators are lauryl peroxide, tributyl hydroperoxide, and benzoyl peroxide (BPO).

The dual-cure system is both self-cure and radiation cure, for example, the self-etching and bonding dental resin cement composition is actinic light curable, specifically ultraviolet (UV) or visible light. Suitable free radical polymerization initiators for visible light-curable compositions employ light-sensitive compounds, including for example, benzil, benzoin, benzoin methyl ether, DL-camphorquinone (CQ), and benzil diketones. Suitable commercially available phosphine oxide photoinitiators include, for example, the LUCIIN™ series from BASF Corp. such as LUCIRIN™ TPO (L-TPO) and LUCIRIN™ 8809. Other phosphine oxide photoinitiators may be selected from the DAROCUR™ or IRGACURE™ series from Ciba-Geigy Corp. Examples include DAROCUR™ TPO, DAROCUR™ 4265, IRGACURE™ 1800, and the like. Either UV-activated cure or visible light-activated cure (approximately 230 to 750 nanometers) is acceptable. The amount of photoinitiator is selected according to the curing rate desired. A minimal catalytically effective amount is generally about 0.01 weight percent of the total self-etching and bonding dental resin cement composition, and will lead to a slower cure. Faster rates of cure are achieved with amounts of catalyst in the range from greater than about 0.1 to about 5 parts per hundred based on the total of the second polymerizable resin composition of the base paste.

Optionally, an ultraviolet absorber can be used in the curing system in an amount of about 0.05 to about 5.0 parts per hundred based on the total of the polymerizable materials of the first or second polymerizable resin composition, for example of the second polymerizable resin composition of the base paste. Such UV absorbers are useful in the visible light-curable dental restorative materials in order to avoid discoloration of the resin from incident ultraviolet light. Suitable UV absorbers are the various benzophenones, particularly UV-5411 available from American Cyanamid Company.

Free radical-type polymerization accelerators suitable for use in the curing system include the various organic tertiary amines well known in the art. In visible light-curable compositions, the tertiary amines are generally (meth)acrylate derivatives such as dimethylaminoethyl methacrylate and, specifically, diethylaminoethyl methacrylate (DEAEMA) or tertiary aromatic amines such as ethyl 4-(dimethylamino)

benzoate (EDMAB) in an amount of about 0.5 to about 5.0 parts per hundred based on the total of the polymerizable materials of the second polymerizable resin composition of the base paste. In the self-curing compositions, the tertiary amines are generally aromatic tertiary amines, specifically tertiary aromatic amines such as EDMAB, 2[4-(dimethylamino)phenyl]ethanol, N,N-dimethyl-p-toluidine (DMPT), and bis(hydroxyethyl)-p-toluidine (DHEPT). Other exemplary accelerators include aromatic sulfinic acid salts, for example benzenesulfinic acid, sodium salt (BSA.Na). Such accelerators are generally present in an amount of about 0.5 to about 4.0 parts per hundred based on the total of the polymerizable materials of the second polymerizable resin composition of the base paste.

The self-etching and bonding dental resin cement composition further comprises a filler system comprising one or more of the inorganic fillers suitable for use in dental composite materials. Examples of suitable filling materials include but are not limited to, silica including fumed silica, quartz, strontium silicate, strontium borosilicate, lithium silicate, lithium alumina silicate, amorphous silica, ammoniated or deammoniated calcium phosphate, tricalcium phosphate, alumina, zirconia, tin oxide, titania, barium-boro-silicate glass filler, glass ionomer filler (e.g. Ca—Al—F—Ba-Silicate) and a combination comprising at least one of the foregoing fillers. Some of the aforementioned inorganic filling materials and methods of preparation thereof are known in the art, as disclosed in U.S. Pat. No. 4,544,359 and No. 4,547,531 to Waknine, pertinent portions of which are incorporated herein by reference. Organic-inorganic fillers of POSS™ (Hybrid Plastics) can be incorporated into the composites as disclosed in U.S. Patent Application Publication 2002/0198282 A1. Other organic-inorganic fillers such as zirconium methacrylate and zirconium dimethacrylate under the codes of CXZRO50 and CXZRO51 (Gelest, Inc.) can also be used. Suitable high refractive index filler materials such as high refractive index silica glass fillers; calcium silicate based fillers such as apatites, hydroxyapatites or modified hydroxyapatite compositions may also be used. Alternatively, inert, non-toxic radiopaque materials such as bismuth oxide ($Bi_2O_3$), bismuth oxychloride (BiOCl), zirconium oxide, barium sulfate, and bismuth subcarbonate in micro- or nano-scaled sizes may be used. In addition, fibrous fillers such as those disclosed in U.S. Pat. Nos. 6,013,694, 6,403,676 and 6,270,562 to Jia and Jia et al. may also be used.

Suitable fillers have particle sizes of about 0.01 to about 5.0 micrometers, and may further comprise bound or unbound silicate colloids of about 0.001 to about 0.2 micrometers. These additional fillers may also be treated with a silane-coupling agent to increase adhesion with the polymerizable (meth)acrylate. Commercially available silane treated fumed silica based on Aerosil A200 can be obtained from Degussa Corp under the names of Aerosil R711 and R7200.

The amount of total filler system in the self-etching and bonding dental resin cement composition can vary from about 30 to about 80 weight percent based on the total weight of the resin cement composition, specifically about 40 to about 70 weight, and more specifically about 50 to about 65 weight percent filler based on the total self-etching and bonding dental resin cement composition.

The amount of filler system in the catalyst paste can be about 1 to about 80 weight percent based on the total weight of the cement composition, specifically about 20 to about 60 weight percent, and more specifically about 30 to about 50 weight percent based on the total weight of the cement composition. The amount of filler system in the base paste can be about 1 to about 80 weight percent based on the total weight of the cement composition, specifically about 20 to about 60 weight percent, and more specifically about 30 to about 50 weight percent based on the total weight of the cement composition.

Any of the present compositions may further include additional additives such as stabilizers (e.g. 3,5-di-tert-butyl-4-hydroxytoluene (BHT)), flavoring agents, disinfectants/medicates, color indicators, pH indicators, a fluoride source, tooth mineralization promoting agent and the like. Suitable fluoride sources include, for example, sodium fluoride, stannous fluoride, sodium monofluorophosphate, calcium fluorophosphate, and the like. When present, fluoride-releasing compounds, excluding the glass ionomer filler, are used in quantities of up to about 2% by weight of the total self-etching and bonding dental resin cement composition.

The self-etching and bonding dental resin cement composition is formulated as a two-paste system where the two pastes are combined prior to use. The catalyst paste contains a polymerizable (meth)acrylate trimellitic acid/anhydride, a phosphoric acid (meth)acrylate, a hydroxyalkyl(meth)acrylate, one or more copolymerizable multi-functional (meth)acrylates, a filler, and a peroxide free radical polymerization initiator; and the base paste contains one or more copolymerizable multi-functional (meth)acrylates, a diluent, a filler, a free radical polymerization accelerator, optionally a polymerizable (meth)acrylate trimellitic acid/anhydride, and optionally a free radical polymerization initiator for visible/ultraviolet light polymerization. Each or either paste may further optionally comprise a stabilizer and/or a UV absorber as long as the stability of the resulting individual paste is not compromised. The filler may include radiopaque materials and high refractive index fillers as described above.

When necessary, desired amounts of the two pastes are metered out and then mixed using a spatula or other appropriate blending equipment. The self-etching and bonding dental resin cement composition thus obtained is then placed in the tooth to be restored.

Use of the self-etching and bonding dental resin cement composition includes applying the self-etching and bonding dental resin cement composition to the tooth or the internal surface of a dental restoration being bonded, adhering the restoration onto the tooth surface, and allowing the cement composition to cure. The self-etching and bonding dental resin cement composition can be self-curable or dual curable (i.e., both self and light curable). The cure may be initiated through the use of actinic radiation, by raising the temperature of the mixture, or by simply waiting for the chemical self-cure that initiates upon mixing the catalyst paste with the base paste. A separate etching step or bonding step (e.g., application of a polymerizable dental adhesive system) need not be performed. The dental resin cement bonds to the tooth without the need for the tooth to be washed.

Useful dental restorative materials or cements that may be used together with the self-etching and bonding dental resin cement compositions include amalgam and non-amalgam dental restoratives. Examples of useful non-amalgam materials include composite resin restoratives, metal and metal alloy restoratives, ceramic/porcelain restorative, and the like. Suitable dental restoratives are those conventional in the art.

The self-etching and bonding dental resin cement composition when applied to a tooth enhances the adhesiveness of the tooth without the need for an etching or bonding step. The multi-step bonding protocols typical of current commercial resin cement systems generally tend to be a source of material waste and unreasonable technique sensitivity. The present self-etching and bonding dental resin cement composition not only reduce the number of steps normally involved in preparing a substrate surface and applying the dental restorative materials, but less waste and improved restorative or sealant results are obtained.

Furthermore, although conventional aggressive etchants are effective in cleaning the surface of dentin for improved wetting, they can also weaken the underlying sound dentin by excessive demineralization and disruption of collagen fibrils. These types of etchants typically require an aqueous rinse step to remove residual acid and soluble by-products. Also, the depth of demineralized, altered dentin resulting from the use of aggressive etchants may exceed the depth to which an adhesive resin can penetrate the dentin, resulting in a weakened, partially reinforced hybrid dentin zone, and thereby become vulnerable to failure. In contrast, the present compositions do not require the use of these etchants and are used as single step composition.

In one embodiment, the self-etching and bonding dental resin cement composition is substantially free of added water. As used herein "substantially free of added water" means that no water is purposely added to the cement compositions and excludes water present in the starting materials or absorbed from the surrounding environment.

Contemplated herein are prepackaged dual-syringe or dual-barrel cartridges containing the self-etching and bonding dental resin cement composition in the form of a two-paste system. Each paste is packaged containing a catalyst paste in one cartridge or syringe and a base paste in the other cartridge or syringe. The two pastes remain separated until use, each paste can be dispensed in the desired amounts, typically equal amounts, mixed together and applied. The prepackaged cartridges may further comprise printed instructions, guidelines or tips for mixing, dispensing, or measuring the components; and/or guidelines for use.

The following non-limiting examples illustrate the invention.

EXAMPLES

Materials used for the following examples include:

| Material | Description |
| --- | --- |
| 4-MET/4-META | 4-Methacryloyloxyethyltrimellitic anhydride from Polyscience, Inc. PA |
| GPMA | Glyceryl dimethacrylate phosphate |
| UDMA | Urethane dimethacrylate |
| HEMA | 2-Hydroxyethyl methacrylate |
| TEGDMA | Tri(ethylene glycol) dimethacrylate |
| BPO | Benzoyl peroxide |
| DHEPT | Bis(hydroxyethyl)-p-toluidine |
| EDMAB | Ethyl 4-(dimethylamino)benzoate |
| Lucirin-TPO | Phosphine oxide photoinitiator from BASF Corp. |
| UV-5411 | Benzophenone UV absorber from American Cyanamid Company |

-continued

| Material | Description |
| --- | --- |
| BHT | 3,5-Di-tert-butyl-4-hydroxytoluene |
| BSA.Na | Benzenesulfinic acid sodium salt |
| CQ | DL-camphorquinone |
| Ba-b-silicate glass filler | Silane treated barium-borosilicate glass filler |
| Glass ionomer filler | Surface active Ca—F—Al—Ba-silicate glass filler |
| Fumed silica | Amorphous/fumed silica filler |

Examples 1-5

In Examples 1-5, a self-etching and bonding dental resin cement composition was prepared from 4-META, GPDM, HEMA, UDMA, and TEGDMA according to the formulas of Tables 1 and 2. The examples are self-etching and bonding dental resin cement compositions prepared from a two-paste system, a catalyst paste and a base paste. For use as a dental cement, the gel (working) time and setting time of the composition is about 2-4 minutes and 5-8 minutes, respectively, when the base paste and catalyst paste are mixed in 1:1 ratio by volume and the material is not subject to a second curing process. In dual-cure mode, when the material, upon mixing the base paste and catalyst paste, is subject to a dental visible light-curing source, the mass of the material will harden immediately upon the photoinitiation.

Table 1 provides the base paste used in each of Examples 1 to 5.

TABLE 1

| | Base Paste |
| --- | --- |
| Base Resin: | UV-5411 1.2 wt %, Lucirin-TPO 0.25 wt %, DHEPT 0.5 wt %, EDMAB 0.4 wt %, CQ 0.2 wt % in UDMA/TEGDMA (wt Ratio: 70/30) |
| Base paste: | Base resin: 32 wt % Filler: 68 wt % total of fumed silica, Ba-b-silicate glass filler, glass ionomer filler, and BSA.Na |

Catalyst resin and paste formulations are provided in Table 2 (all components are in parts per hundred) as well as the properties of the cement composition upon mixing the catalyst and base pastes in a 1:1 ratio.

TABLE 2

Self-Etching and Bonding Dental Resin Cement Composition Containing
4-methacryloyloxyethyltrimellitic Anhydride

|  |  | EXAMPLE 1 Catalyst 1 | EXAMPLE 2 Catalyst 2 | EXAMPLE 3 Catalyst 3 | EXAMPLE 4 Catalyst 4 | EXAMPLE 5 Catalyst 5 |
|---|---|---|---|---|---|---|
| Resin Components | | | | | | |
| 4-META | | 40 | 40 | 40 | 30 | 20 |
| GPDM | | 10 | 10 | 10 | 10 | 12 |
| HEMA | | 20 | 13 | 13 | 15 | 10 |
| UDMA | | 0 | 10 | 10 | 20 | 33 |
| TEGDMA | | 30 | 27 | 27 | 25 | 25 |
| BPO | | 2.5 | 2.5 | 2.5 | 2.5 | 2.5 |
| BHT | | 0.2 | 0.2 | 0.2 | 0.2 | 0.2 |
| Paste Composition | | | | | | |
| Catalyst resin mix | | 33 | 33 | 33 | 34 | 34 |
| Fumed silica | | 0.3 | 0.3 | 0.3 | 0.5 | 0.5 |
| Ba-b-silicate glass filler | | 66.7 | 66.7 | 66.7 | 65.5 | 65.5 |
| Property | | | | | | |
| Gel Time (min:sec) | | 3:10 | 4:00 | 4:00 | 3:30 | 2:00 |
| Set Time (min:sec) | | 5:10 | 8:00 | 8:00 | 7:00 | 5:00 |
| SBS to dentin, MPA (S.D.) | | 11.07 (4.12) | 15.10 (5.16) | 15.07 (3.73) | 14.82 (6.18) | 12.43 (3.95) |
| Linear Expansion (%): | | | | | | |
| SC* | 1 month | 1.1 | 0.77 | 0.75 | 0.73 | 0.72 |
|  | 2 months | 1.22 | 0.99 | 1.05 | 0.88 | 0.76 |
|  | 3 months | 1.24 | 1.03 | 1.06 | 0.98 | 0.84 |
| DC* | 1 month | 0.93 | 0.95 | 0.76 | 0.76 | 0.83 |
|  | 2 months | 0.99 | 1.24 | 1.03 | 1.03 | 0.85 |
|  | 3 months | 1.06 | 1.37 | 1.26 | 1.06 | 1.00 |

*SC = self-cured only; DC = dual cured (i.e., both light and self-cured).

The bonding test method was as follows:
1. 3G® ceramic rods were fabricated with a dental porcelain furnace according to the ceramic firing temperature and conditions of the product. The 3G® ceramic rods used for the bonding test have final dimensions of about 3.2 mm diameter and 6-8 mm length, on which one end of the rod was sandblasted, cleaned and then silane treated as per the product instructions. The treated end will be contacting the bonding cement as in a tooth restoration. Each test group contained 5 samples.
2. Teeth samples were prepared to expose the dentin and then the teeth were mounted with an acrylic material leaving the dentin exposed, which were then subject to sand paper grinding under wet condition to have a same surface pattern for all the test groups.
3. The base paste and catalyst past of Examples 1-5 were mixed in equal amounts and applied onto the prepared, briefly dried tooth surface. The ceramic rod was then seated onto the cement surface under a 500 gram load with the aid of a BenCor Multi-test device (Danville Engineering, CA).
4. After the cement hardened, the bonded samples were transferred into a 100% humidity chamber held at 37° C. for 24 hours before the debond test.
5. The debond test was done in push shear mode using a BenCor testing device on an ATS testing machine. The load at which the bonded ceramic rod broke was recorded and the shear bonding strength of the testing sample was then calculated based on the rod surface area. Standard deviation is reported in parentheses.

From the property results above, it is observed that, with the addition of the GPDM resin into the catalyst composition, the amount of 4-META and HEMA resins in the catalyst resin compositions can be reduced. Surprisingly, the performance of the resulting materials is synergized, as least in some aspects. For example, the water absorption and solubility of the mixed two-part self-cured materials are greatly improved. That property is important in maintaining the mass integrity and reducing hydroscopic expansion stress during the service of the material intra-orally, while the material can still cure in self-cure mode with the phosphoric acid resin and BPO initiator co-existing in the same composition.

As a comparison, the cement formula disclosed in U.S. Pat. No. 6,730,715 to Jia was used as a bonding reference. The dentin bonding strength of the comparison material tested according to the method described above is in the range of 3-8 MPa, while the present cement compositions containing 4-META/GPDM have significantly greater bonding strengths and on the same order as that disclosed in the parent to this application, U.S. Pat. No. 7,906,564. The formula in U.S. Pat. No. 7,906,564 mainly has 4-META and HEMA in the catalyst resin formulation, which are very hydrophilic in nature. The present formula minimizes the use of 4-META by replacing part of 4-META with GPDM to keep the overall hydrophilic monomers less while maintaining the same acidity. The linear hydroscopic expansion measured is about 30% less than the Examples in U.S. Pat. No. 7,906,564. And, contrary to what is expected, the stability of the BPO/amine initiating system remains good and adequate for commercial use despite the additional presence of the highly acidic phosphoric acid-containing resin.

The terms "a" and "an" do not denote a limitation of quantity, but rather denote the presence of at least one of the referenced item. The terms "first," "second," and the like, "primary," "secondary," and the like, as used herein do not denote any order, quantity, or importance, but rather are used to distinguish one element from another. "Optional" or "optionally" means that the subsequently described event or circumstance may or may not occur, and that the description includes instances where the event occurs and instances where it does not. The endpoints of all ranges directed to the same component or property are inclusive and independently combinable.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A self-etching and bonding dental resin cement composition, comprising:
a two-paste system that is combined prior to use, wherein a first catalyst paste comprises a first polymerizable resin composition, a first filler, and a peroxide free radical polymerization initiator, and wherein a second base paste comprises a second polymerizable resin, a second filler, a free radical polymerization accelerator, and optionally a photoinitiator,
wherein the first polymerizable resin composition comprises, based on 100 weight percent:
about 5 to about 50 weight percent of a polymerizable (meth)acrylate trimellitic acid/anhydride selected from 4-(meth)acryloyloxymethyltrimellitic acid; 4-(meth)acryloyloxymethyltrimellitic anhydride; 4-(meth)acryloyloxyethyltrimellitic acid; 4-(meth)acryloyloxyethyltrimellitic anhydride; 4-(meth)acryloyloxypropyltrimellitic acid; 4-(meth)acryloyloxypropyltrimellitic anhydride; or a combination thereof;
about 5 to about 20 weight percent of a phosphoric acid (meth)acrylate;
about 5 to about 25 weight percent of a hydroxyalkyl (meth)acrylate; and
the balance being one or more first copolymerizable multi-functional (meth)acrylates, and
wherein the second polymerizable resin composition comprises, based on 100 weight percent:
about 50 to about 95 weight percent of one or more second copolymerizable multi-functional (meth) acrylates; and
about 5 to about 50 weight percent diluent.

2. The composition of claim 1, wherein the first polymerizable resin composition comprises about 20 to about 40 weight percent of the polymerizable (meth)acrylate trimellitic acid/anhydride.

3. The composition of claim 2, wherein the polymerizable (meth)acrylate trimellitic acid/anhydride is 4-methacryloyloxyethyltrimellitic anhydride.

4. The composition of claim 1, wherein the first polymerizable resin composition comprises about 10 to about 15 weight percent of the phosphoric acid (meth)acrylate.

5. The composition of claim 4, wherein the phosphoric acid (meth)acrylate is glyceryl dimethacrylate phosphate.

6. The composition of claim 1, wherein the first polymerizable resin composition comprises about 10 to about 20 weight percent of the hydroxyalkyl(meth)acrylate.

7. The composition of claim 1, wherein the hydroxyalkyl (meth)acrylate is 2-hydroxyethyl methacrylate.

8. The composition of claim 1, wherein the one or more first and second copolymerizable multi-functional (meth) acrylates are independently selected from a urethane (meth) acrylate, a urethane di(meth)acrylate; a polyurethane(meth) acrylate; a diurethane dimethacrylate; a polycarbonate di(meth)acrylate; an ethoxylated bisphenol A di(meth)acrylate; an ethoxylated trimethylolpropane tri(meth)acrylate; a diglycidyl (meth)acrylate adduct of Bisphenol A; or a combination thereof.

9. The composition of claim 1, wherein the one or more first copolymerizable multi-functional (meth)acrylates comprise tri(ethylene glycol) dimethacrylate and/or urethane dimethacrylate.

10. The composition of claim 1, wherein the one or more second copolymerizable multi-functional (meth)acrylates comprise urethane dimethacrylate, and the diluent comprises tri(ethylene glycol)dimethacrylate.

11. The composition of claim 1, wherein the first catalyst paste further comprises a stabilizer; and wherein the second base paste further comprises the photoinitiator and an ultraviolet absorber.

12. The composition of claim 1, wherein the peroxide free radical polymerization initiator is benzoyl peroxide.

13. The composition of claim 12, wherein the second base paste comprises the photoinitiator, and the free radical polymerization accelerator comprises a plurality of free radical polymerization accelerators including at least two aromatic tertiary amines and at least one aromatic sulfinic acid salt.

14. The composition of claim 1, wherein the self-etching and bonding dental resin cement composition is substantially free of added water.

15. A self-etching and bonding dental resin cement composition, comprising:
a dual-cure two-paste system that is combined prior to use, wherein a first catalyst paste comprises a first polymerizable resin composition, a first filler, and a benzoyl peroxide free radical polymerization initiator, and wherein a second base paste comprises a second polymerizable resin, a second filler, a free radical polymerization accelerator, and a photoinitiator,
wherein the first polymerizable resin composition comprises, based on 100 weight percent:
about 5 to about 50 weight percent of a polymerizable (meth)acrylate trimellitic acid/anhydride selected from 4-(meth)acryloyloxymethyltrimellitic acid; 4-(meth)acryloyloxymethyltrimellitic anhydride; 4-(meth)acryloyloxyethyltrimellitic acid; 4-(meth) acryloyloxyethyltrimellitic anhydride; 4-(meth)acryloyloxypropyltrimellitic acid; 4-(meth)acryloyloxypropyltrimellitic anhydride; or a combination thereof;
about 5 to about 20 weight percent of glyceryldimethacrylate phosphate;
about 5 to about 25 weight percent of a hydroxyalkyl (meth)acrylate selected from 2-hydroxyethyl(meth) acrylate, 2-hydroxypropyl(meth)acrylate, or 4-hydroxybutyl(meth)acrylate; and
the balance being one or more first copolymerizable multi-functional (meth)acrylates selected from tri (ethylene glycol) dimethacrylate and/or urethane dimethacrylate, and
wherein the second polymerizable resin composition comprises, based on 100 weight percent:
about 50 to about 95 weight percent of one or more second copolymerizable multi-functional (meth) acrylates; and
about 5 to about 50 weight percent diluent.

16. The composition of claim 15, wherein the one or more second copolymerizable multi-functional (meth)acrylates comprise urethane dimethacrylate, and the diluent comprises tri(ethylene glycol) dimethacrylate.

17. The composition of claim 15, wherein the first catalyst paste further comprises a stabilizer; and wherein the second base paste further comprises an ultraviolet absorber.

18. The composition of claim 15, wherein the self-etching and bonding dental resin cement composition is substantially free of added water.

19. A method of restoring a tooth, comprising:
mixing the first catalyst paste and the second base paste of claim 1 to form a self-etching and bonding dental resin cement composition;
applying the self-etching and bonding dental resin cement composition to a tooth surface or a surface of a dental restoration being bonded without the use of any additional etching or bonding step prior to the applying;
applying a dental restorative material; and
curing the cement composition.

20. A method of restoring a tooth, comprising:
mixing the first catalyst paste and the second base paste of claim 15 to form a self-etching and bonding dental resin cement composition;
applying the self-etching and bonding dental resin cement composition to a tooth surface or a surface of a dental restoration being bonded without the use of any additional etching or bonding step prior to the applying;
applying a dental restorative material; and
curing the cement composition with actinic light.

* * * * *